350-96.15
5/26/81   XR   4,270,049   SR

United States Patent [19]
Tanaka et al.

[11] 4,270,049
[45] May 26, 1981

[54] LIQUID LEAKAGE DETECTION SYSTEM

[75] Inventors: Masaya Tanaka, Tokyo; Mitsuo Ono, Koganei; Sadao Degawa, Tanashi, all of Japan

[73] Assignee: Ishikawajima-Harima Jukogyo Kabushiki Kaisha, Tokyo, Japan

[21] Appl. No.: 47,208

[22] Filed: Jun. 11, 1979

[30] Foreign Application Priority Data

Jun. 12, 1978 [JP] Japan ................................. 53-70660
Jun. 12, 1978 [JP] Japan ................................. 53-70661
Jun. 12, 1978 [JP] Japan ................................. 53-70662
Jun. 12, 1978 [JP] Japan ............................ 53-80296[U]
Jul. 12, 1978 [JP] Japan ............................ 53-95914[U]

[51] Int. Cl.$^3$ ............................................... G02B 5/16
[52] U.S. Cl. ..................................... 250/227; 250/577; 340/605; 350/96.15; 350/96.30; 356/70
[58] Field of Search ...................... 250/574, 577, 227; 350/96.29, 96.30, 96.33, 96.21, 96.15; 73/293; 356/133, 70; 340/605

[56] References Cited

U.S. PATENT DOCUMENTS

| | | | |
|---|---|---|---|
| 3,383,863 | 5/1968 | Berry | 340/605 X |
| 3,564,526 | 2/1971 | Butts | 340/605 X |
| 3,721,898 | 3/1973 | Dragoumis et al. | 340/605 X |
| 4,045,668 | 8/1977 | Pitt et al. | 250/227 |
| 4,118,105 | 10/1978 | Voigt | 250/227 |
| 4,159,420 | 6/1979 | Tsunoda | 250/227 |

OTHER PUBLICATIONS

Pliskin, "Refractive Index Lowering of the Cladding for Optical Fiber Waveguides"; IBM Technical Disclosure Bulletin, vol. 18, No. 5, Oct. 1975.
Someda, "Simple Low-Loss Joints Between Single-Mode Optical Fibers"; Bell System Tech. Journal, vol. 52, No. 4; Apr. 1973.

*Primary Examiner*—David C. Nelms
*Assistant Examiner*—Edward P. Westin
*Attorney, Agent, or Firm*—Alfred E. Miller

[57] ABSTRACT

Leakage of a liquid may be detected in terms of the drop in intensity of light rays traveling through a light guide core or optical fiber made of glass or synthetic resins due to the adhesion of the leaked liquid to the light guide.

9 Claims, 25 Drawing Figures

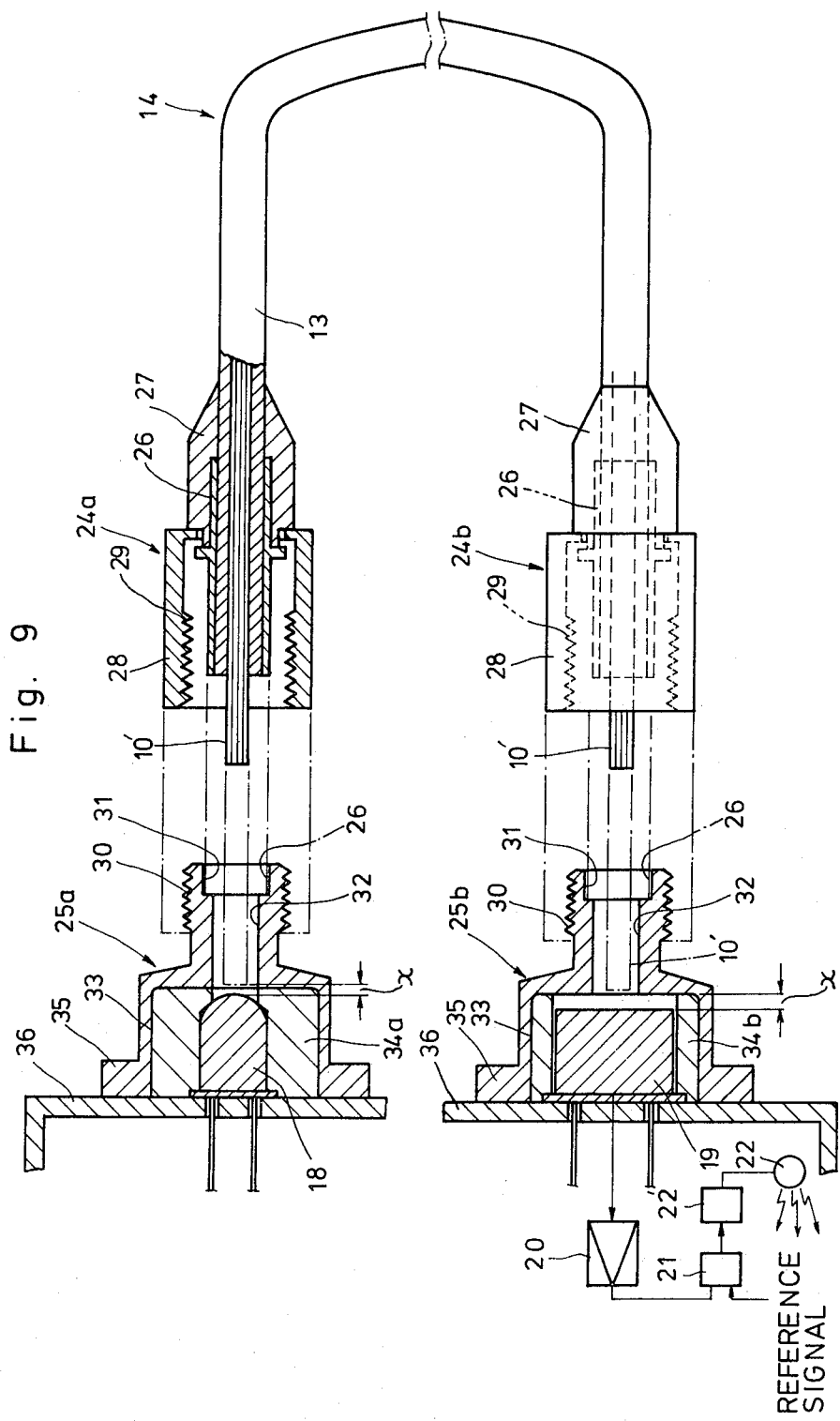

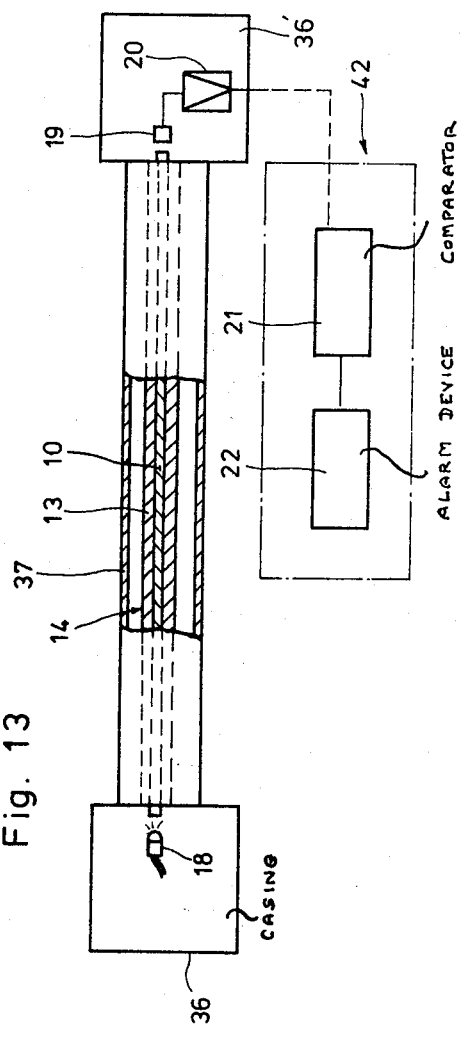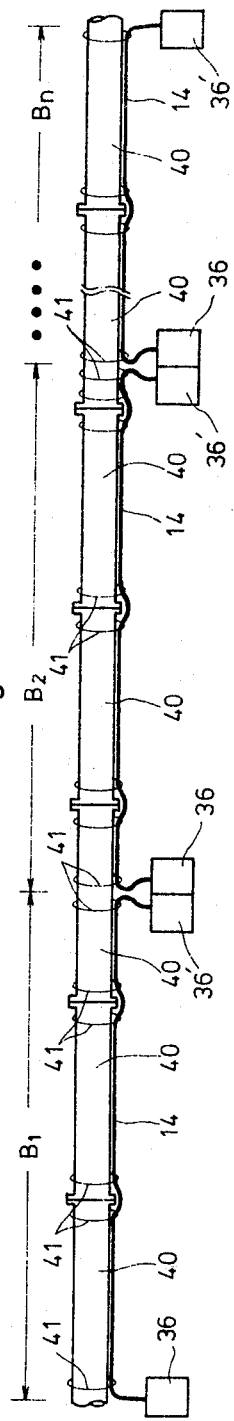
Fig. 13
Fig. 14

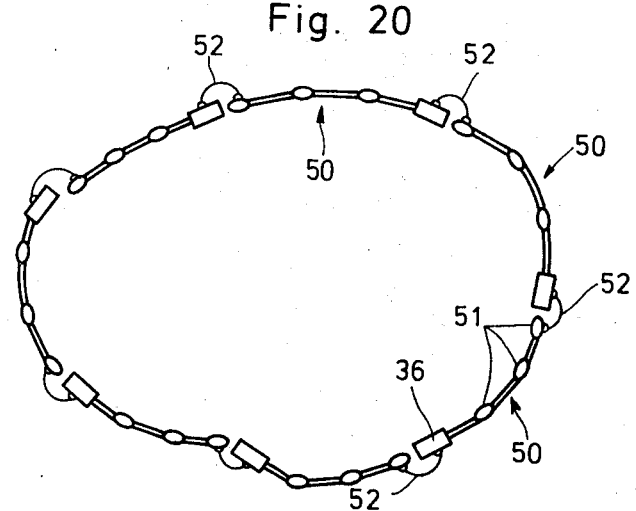
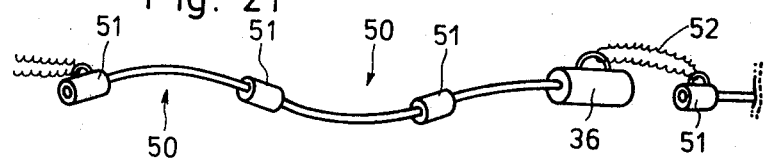
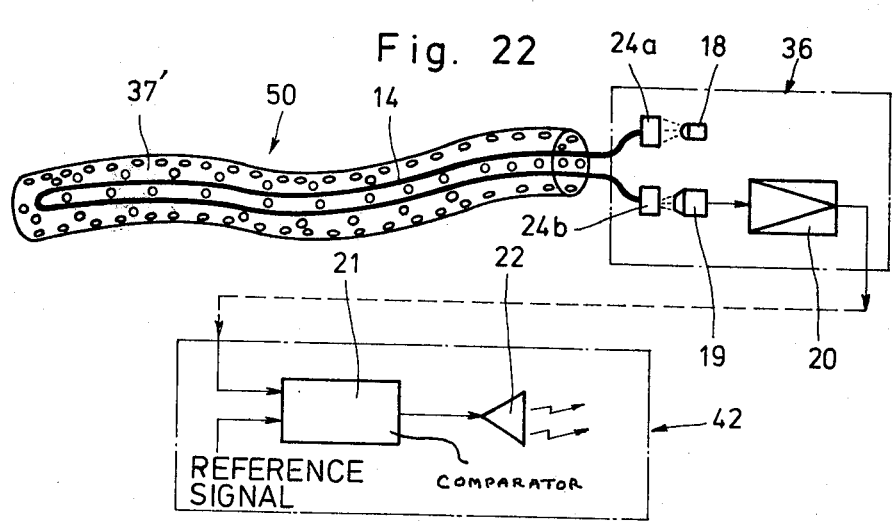

LIQUID LEAKAGE DETECTION SYSTEM

BACKGROUND OF THE INVENTION

The present invention relates to a liquid leakage detection system.

Accidents in which crude oil leaks from storage tanks, or other oils and hazardous liquids leak from chemical plants have been increasing and the contamination of the sea, rivers and lakes due to the leakage of various oils and other hazardous liquids have also been on the increase. As a result, pollution control standards and emission control regulations have been instituted and enforced by authorities so that devices and systems capable of detecting leakages of oils and other hazardous liquids must be installed. These liquid leakage detection devices or systems must have a high reliability and must be dependable in operation, so that any leakage may be immediately and accurately detected.

In FIG. 1 a prior art structure is shown which is a liquid leakage detection device of electrical capacitance type. A float 1 is shown floating in a sump or reservoir, or is disposed at a predetermined level in a pit which is emptied. Electrodes 3 are attached to the interior wall surface of the float 1 at a position corresponding to the water line 2 of the float 1, and a weak, high-frequency signal from an electronic circuit 4 is normally applied to the electrodes. When no oil is leaking, the high-frequency current applied to the electrodes 3 is dissipated through the wall, which is fabricated by synthetic resins into the water or a stand (not shown). When the leaking oil flows into the sump, reservoir or pit, the effective dielectric constant of the wall adjacent to the electrodes 3 varies due to the adhesion of the oil 5 to the wall. As a result, the high-frequency current dissipation is reduced and is detected by the electronic circuit 4. In response to the detection signal transmitted through a cable 6 from the electronic circuit 4, an alarm device (not shown) is actuated to give visual and/or sound alarms. The water-line of the float 1 and hence the position of the electrodes 3 may be adjusted by selecting a suitable weight 7 to be placed in float 1.

However, the oil leakage detection device of the type described above cannot detect the leakage of oil until the oil, which has leaked accumulates to relatively great volume. That is, the response is so slow that suitable countermeasures against the oil leakage cannot be taken quickly. Furthermore, the prior art detection device cannot pinpoint a leaking place. Moreover, since the float is placed in the oil, it must be explosion-proof.

Accordingly, one of the objects of the present invention is to provide a liquid leakage detection system which may substantially overcome the above and other problems encountered in the prior art liquid leakage detection devices and a system which is very simple in construction yet highly reliable in operation.

The present invention will become apparent from the following description of some preferred embodiments thereof taken in conjunction with the accompanying drawings.

BRIEF DESCRIPTION OF THE DRAWINGS

FIG. 5 is a perspective view of an oil detector cable used in the first embodiment of the present invention;

FIG. 6 is a sectional view thereof;

FIG. 7 is a side view of an oil storage tank on which the oil detector cables are attached;

FIG. 8 is a top plan view of FIG. 7;

FIG. 9 is a sectional view used for the explanation of a second embodiment of the present invention;

FIG. 10 is a perspective view of the third embodiment;

FIG. 11 is a perspective view of an oil storage tank equipped with the oil detector cables;

FIG. 12 is a view showing the connection of each oil detector cable to a monitor station;

FIGS. 13 and 14 are mainly elevational views used for the explanation of a forth embodiment of the present invention;

FIG. 13 is a side elevational view, partly in section, of an oil detector cable;

FIG. 14 is a side elevational view showing the oil detector cables attached to a pipeline;

FIGS. 16-19 are views used for the explanation of a sixth embodiment of the present invention in which;

FIG. 16 is a perspective view of an oil detector mat used in the sixth embodiment of the present invention;

FIG. 17 is a perspective view showing the oil detector mat attached to the flange joint of pipe sections so as to detect the oil leakage through the joint;

FIG. 18 is a perspective view of a modification of an oil detector mat.

FIG. 19 is a sectional view taken along the line XIX—XIX of FIG. 18;

FIGS. 20-22 are views used for the explanation of a seventh embodiment of the present invention in which;

FIG. 20 is a perspective view of an oil detection fence consisting of oil detectors connected into a ring form;

FIG. 21 is a perspective view of one oil detector;

FIG. 22 is a detailed view thereof with its associated electronic circuits;

Figure 1:
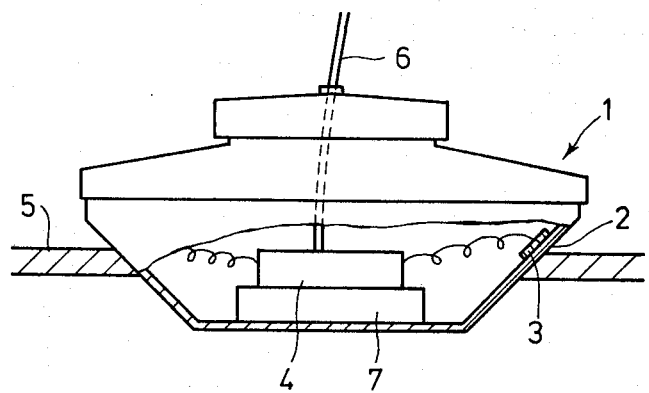
FIG. 1 is a schematic side view, partly broken away, of a prior art liquid leakage detection device.
Figure 2:
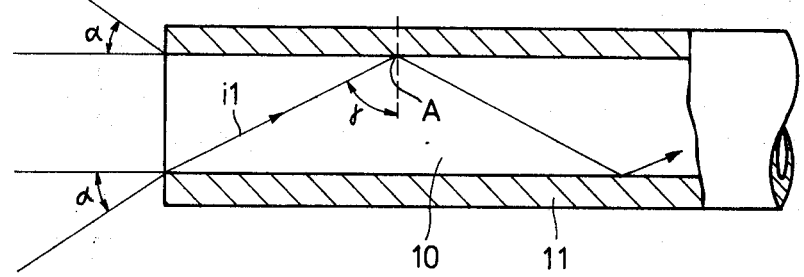
FIGS. 2 and 3 are sectional views of a light guide used for the explanation of the underlying principle of the present invention.
Figure 3:
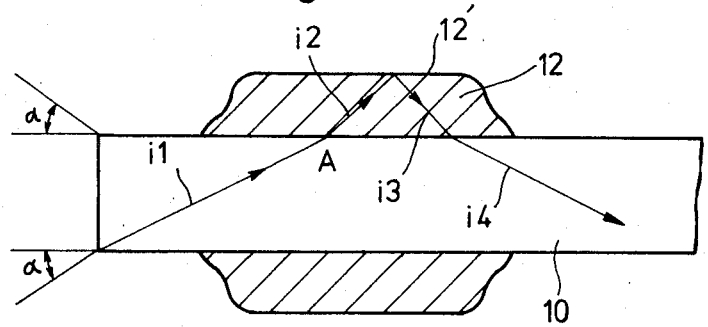

Referring first to FIGS. 2 and 3, a light guide used in the present invention will be described. The light guide consists of a plurality of optical fibers each consisting of a core which carries the light rays and a cladding which is an outer layer that traps the rays in the core. The core is made of glass or synthetic resins. The light signal applied to one end of the light guide may travel to the other end with a minimum transmission loss.

One optical fiber is shown in FIG. 2. The index of refraction $n_1$ of the core 10 is selected higher than that $n_2$ of the cladding 11. A light ray entering into one end of the light guide core 10 at an angle less than an acceptance angle $\alpha$ which is dependent upon a critical angle $\gamma$ at the interface between the light guide core 10 and cladding 11, repeatedly bounces off the interface and reaches the other end with a minimum transmission loss.

The cladding 11 need not be made of glass or synthetic resins. It may be any medium, such as the air whose index of refraction is defined as unity, having an index of refraction lower than that $n_1$ of the light guide core 10. Therefore, the light guide core 10 shown in FIG. 3 may be considered as being cladded with air. When an optical medium 12 whose index of refraction $n_3$ is higher than that of the light guide core 10 adheres to the exterior surface of the light guide core 10, a light ray $i_1$ which has been propagating through the light guide core 10 cannot bounce off at the point A so that it passes through the interface between the light guide core 10 and the cladding, which is the air, as indicated by a light path $i_2$ into the optical medium 12. When the optical medium 12 is crude or heavy oil which has a relatively high absorption coefficient, the light ray is almost absorbed so that the energy of a light ray bounced off at the interface 12' between the optical medium 12 and the air and passing along the paths $i_3$ and $i_4$ is considerably reduced. Therefore, the attachment or adhesion of an oil drop to the light guide core 10 may be detected in terms of the variations of the intensity of the light ray emerging from the other end of the light guide core 10. When the cladding 11 is made of materials which may be easily attacked by crude or heavy oil, the adhesion of crude or heavy oil to the light guide may be detected in a manner substantially similar to that described above. This is the underlying principle of the present invention.

As described in the explanation of FIG. 3, the air may be used in theoretically as a cladding, but under some environmental conditions certain matter, other than the oil, attach to the light guide core 10 so that malfunctions occur. Therefore, it follows that the light guide core 10 must be cladded with materials other than the air (or gases). The separation of the cladding from the light guide core 10 must be prevented, but the cladding must not be strong enough to prevent the oil to pass through it and reach the exterior surface of the light guide core 10.

Figure 4:
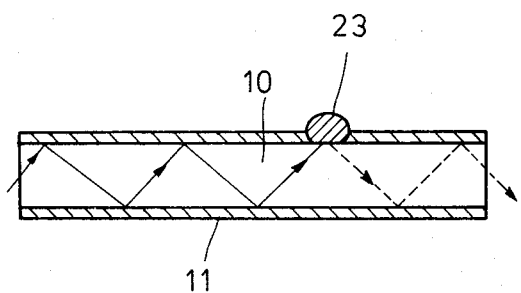
FIG. 4 is a sectional view used for the explanation of a cladding which surrounds a light guide used in the present invention.

In view of the above, according to the present invention, the cladding 11 as shown in FIG. 4 is made of materials which may be easily attacked and/or swollen when they are contacted by oil. For instance, the cladding 11 is made of silicon resins, and when the leakage of petroleum oil, such as crude oil, heavy oil and gasoline are detected. An oil drop 23 as seen in FIG. 4 adheres to the exterior surface of the cladding 11 and the cladding 11 is locally damaged, and the oil drop 23 penetrates through the cladding into direct contact with the exterior surface of the light guide core 10. As a result, part of the energy of the light rays transmitted through the light guide core 10 is absorbed by the oil drop 23, as described hereinafter so that the intensity of the light rays intercepted by the optical sensor 19 is reduced.

DESCRIPTION OF THE PREFERRED EMBODIMENTS

Figure 5:
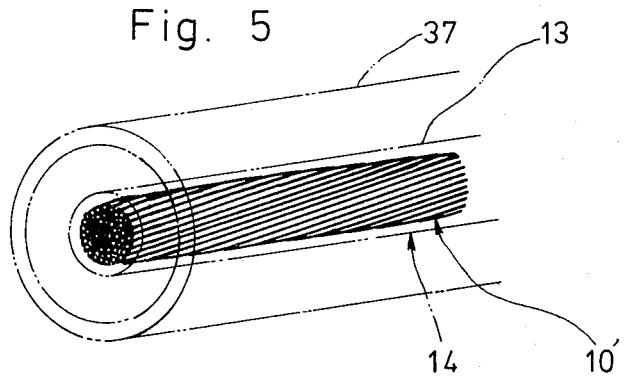
FIGS. 5-8 are views used for the explanation of a first embodiment of the present invention.
Figure 6:
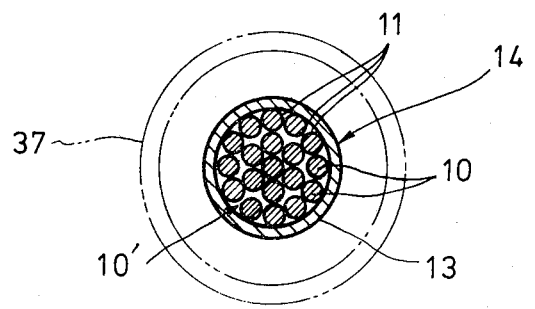

As shown in FIGS. 5 and 6, an oil detector cable 14 consists of the light guide 10', which is formed by a plurality of optical fibers, each of which consists of the light guide core 10 and the cladding 11, and which are stranded or otherwise assembled and coated with a sheath 13. The sheath 13 which serves to absorb oil. For instance, the sheath 13 may be made of cotton or glass cloth, etc.

In situations where it is necessary to protect an oil detector cable 14 from damage, the outer surface of the sheath 13 is surrounded by a protective jacket 37, as shown in FIGS. 5 and 6. For example, the protective jacket 37 may be made of coiled springs, or the like, as ribs, and it is formed as a flexible cylindrical body by knitting and wrapping a braid of a fine-diameter wire members onto the outer surface of the coiled springs, thereby having the nature of liquid permeability and pliability. The protective jacket 37 is not required to be provided, and it may be replaced by other protective means.

Figure 7:
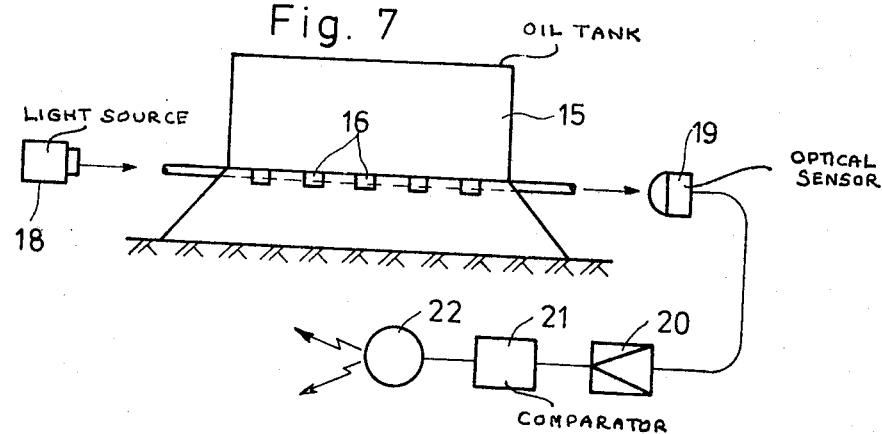
Figure 8:
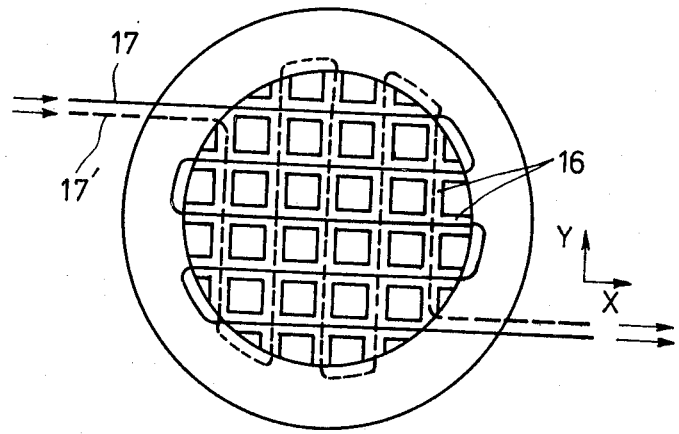

As shown in FIGS. 7 and 8, two oil detector cables 17 and 17' and the protective jacket 37 of the type shown in FIG. 5 are laid in the form of a mesh in a mesh-like cable pits 16, and are provided immediately below the bottom of an oil tank 15. That is, the first oil detector cable 17 is laid in a zig-zag form in the direction indicated by the arrow X while the second oil detector cable 17' is laid in a zig-zag form in the direction indicated by the arrow Y. The ends of the first and second oil detector cables 17 and 17' is positioned adjacent to a light source or light-emitting element 18 while the other ends are positioned adjacent to an optical sensor 19, or are optically connected thereto. The output from the optical sensor 19 is amplified by an amplifier 20 and applied to a comparator 21 which compares the output from the amplifier 20 with a reference signal. When the oil stored in the oil tank 15 leaks and attaches to the first and second oil detector cables 17 and 17' at various points, the intensity of the light rays intercepted by the optical sensor 19 drops below a predetermined level and consequently the input to the comparator 21 drops below a reference level. Then the comparator 21 delivers the output to an alarm device 22 which in turn gives visual and/or audio alarms.

Referring to FIG. 9, female connectors 24a and 24b are attached to the ends of the oil detector cable 14, as shown in FIGS. 5 and 6, for detachable connection with male connectors 25a and 25b, respectively, of the light emitting element 18 and the optical sensor 19. This coupling arrangement may facilitate the replacement of the oil detector cable 14 after the contamination of the oil detector cable 14 with the oil that has leaked and hence the detection of the oil leakage.

Since both the female connections 24a and 24b on the oil detector cable 14 are the same in construction, only the female connection 24a will be described in detail. The female connector 24a consists of a terminal tube 26, a protective tube 27 and a coupling device 28 having internally threaded screw threads 29. The terminal tube 26 is made of metal and fitted a predetermined distance over the end of the sheath 13 of the oil detector cable 14, and securely attached thereto. The protective tube 27, which is made of elastic materials such as rubber, is fitted over the terminal tube 26 and the oil detector cable 14 so as to prevent the break-off of the oil detector cable 14 at the inner end of the terminal tube 26 due to bending. The female coupling member 28 between the end of the protective tube 27 and the guard of the tube 26 is provided over the terminal tube 26 in such a way that the coupling member 28 may freely rotate, but the axial displacement is limited by the engagement of the annular wall at the inner end of the female coupling member 28.

The male connectors 25a and 25b of the light-emitting element 18 and the optical sensor 19 which are shown in section are substantially similar in construction so that only the male connector 25a will be described below. The male connector 25a consists of a small-diameter section and a large diameter section. A male screw thread 30 is provided at the end of the connector 25a, a large-diameter hole 31 receives the terminal tube 26 and a small-diameter hole 32 receives the light guide core assembly 10'. The large-diameter section has an annular flange 35 for mounting the male connector 25a on a casing 36 and a large-diameter hole 33 which is coaxial with the small-diameter hole 32 and receives a collar 34a (34b). The collar 34a has the outer diameter equal to the inner diameter of the large-diameter hole 33 and has the inner diameter equal to the outer diameter of the light-emitting element 18 (the optical sensor 19). The collars 34a and 34b serve not only to attain the correct optical registrations between the ends of the light guide core assembly 10' on the one hand and the light-emitting element 18 and the optical sensor 19 on the other hand, but also ensure the electrical insulation of the light-emitting element 18 and the optical sensor 19. The collars 34a and 34b may be made of synthetic resins.

A power circuit (not shown) for supplying the power to the light-emitting element 18, the amplifier 20 and other associated circuits is located within the casing 36.

The oil detector cable 14 and the casing 36 to which the cable 14 is attached in the manner described above are laid at a place where the oil leakage or the contamination by the oil is desired to be detected. The output signal from the amplifier 20 may be transmitted through a suitable wire or wireless transmission line to a centralized monitor station wherein the incoming signal is applied to the comparator 21 and the alarms are generated in the manner described elsewhere. In the case of the wireless transmission of the output signal from the amplifier 20 to the centralized monitor station, a transmitter (not shown) is of course encased within the casing 36. Moreover, the casing may further include the comparator 21, the alarm circuit 22' and the alarm device 22. When the oil detector cable 14 is folded back as shown in FIG. 9, all the electrical circuits may be encased within the single casing 36, but when the oil detector cable 14 is extended straight, the electric circuits associated with the light-emitting element 18 are encased in one casing 36 while those associated with the optical sensor 19, in another casing 36.

Next the mode of coupling operation will be described. The exposed light guide core assembly 10' at one end of the oil detector cable 14 is first inserted into the small-diameter hole 32 of the male connector 25a as indicated by the one-dot chain line, and then the female coupling member 28 is screwed to the male coupling member; that is, the internally threaded screw 29 are engaged with the externally threaded screw threads 30. The female coupling member 28 is tightened until the leading or outer end of the terminal tube 26 is brought into contact with the bottom of the counter bore at the outer end of the small-diameter hole 32 so that the end of the exposed light guide core assembly 10' may be spaced apart from the light-emitting element 18 (the optical sensor 19) by a predetermined distance $\chi$ correctly.

When the distance $\chi$ is too wide, the efficient launching of the light rays into the core assembly 10' of the oil detector cable 14 cannot be attained. For instance, the female and male connectors 24a and 24b and 25a and 25b are so designed and constructed that when the diameter of the light guide core assembly 10' is 1.2 mm, the distance $\chi$ is from 0.2 to 0.4 mm. In the experiments conducted by the inventors, it was found out that 19 light guide cores 10 with the diameter of 180 micrometers are stranded or otherwise assembled into an assembly or bundle 1.2 mm in diameter.

Figure 10:
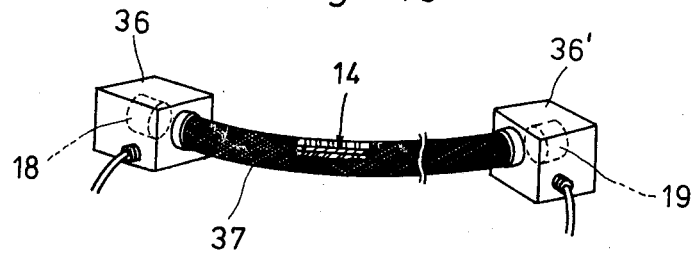
FIGS. 10-12 are schematic views used for the explanation of a third embodiment of the present invention.
Figure 11:
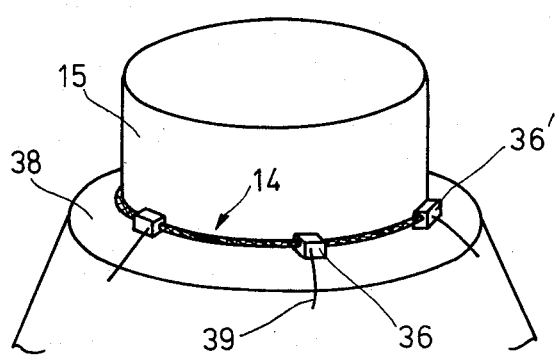
Figure 12:
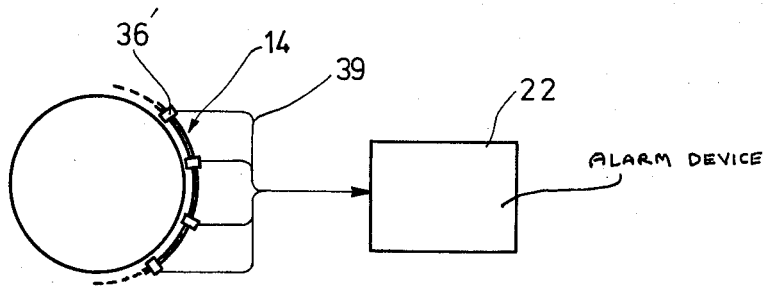

The third embodiment of the present invention shown in FIGS. 10-12 is such that it may surround closely an oil tank for the detection of the leakage of the oil stored therein. The light guide core assembly 10' shown in FIGS. 5 and 6 is sheathed with the sheath 13 so as to form the oil detector cable 14. The oil detector cable 14 is surrounded by the protective jacket 37. For instance, the protective jacket 37 may be made of a braid of stainless coils which are resistive to corrosion, with fine-diameter stainless wires being wrapped around the coils so as to have the nature of porosity and flexibility. The protective jacket 37 is flexible so that the oil detector cable 14 may be attached to any oil storage tanks or vessels of various shapes.

As with the second embodiment described above, the ends of the oil detector cable 14 are physically and optically connected to the housings 36 and 36' containing the light-emitting element 18 and its associated circuits, as well as the optical sensor 19 and its associated circuits, respectively.

As shown in FIG. 10, a plurality of oil detector cables 14 with terminal housings or casings 36 and 36' are connected in series and laid on the foundation 38 of an oil tank 15 shown in FIG. 11 in close contact relationship with its shell wall. Since the shell wall is divided by means of a plurality of oil detector cables 14 into a plurality of sections, any section in which the oil leakage occurs may be immediately and easily detected. When the oil leaks at the bottom of the oil tank, it flows through the space between the bottom of the oil tank 15 and the foundation 38 and reaches one of the oil detector cables 14 surrounding the oil tank 15. The leaking oil further flows through the pores of the protective jacket 37 and reaches the exterior surface of the light guide core assembly 10'. Then, as described elsewhere, the intensity of the light rays received by the optical sensor 19 of the oil detector cable 14 in a certain section at which the oil leakage has occurred, drops below a reference level. Thus, oil leakage in the tank may be detected.

The optical sensors 19 are connected through cables 39 to an alarm device 22. In response to the output signal from the optical sensor 19 of the oil detector cable 14 which has been contaminated by the leaking oil, the alarm device 22 may immediately give audio alarms while simultaneously displaying a section of the oil tank 15 in which oil is leaking.

In FIGS. 13 and 14 are shown the fourth embodiment of the present invention, which is adapted for detecting the leakage of oil in a pipeline or the like. That is, the whole length of the pipeline 40 is divided into a plurality of sections $B_1$-$B_n$ of an equal distance, and one oil detector cable 14 with the housings or casings 36 and 36' is laid for each section B. It is preferable that the oil detector cable 14 may be supported by suitable supporting means 41 such as wires, strings, hangers or the like in direct contact with the pipeline 40. The output signal from the amplifier 20 of each casing 36', which contains the optical detector 19 is transmitted to one or more monitor stations 42 having a plurality of monitor circuits for respective sections $B_1-B_n$, each monitor circuit consisting of the comparator 21 and the alarm device 22. Thus any section $B_1-B_n$ of the pipeline 40 where the oil leakage occurs may be immediately detected.

Figure 15:
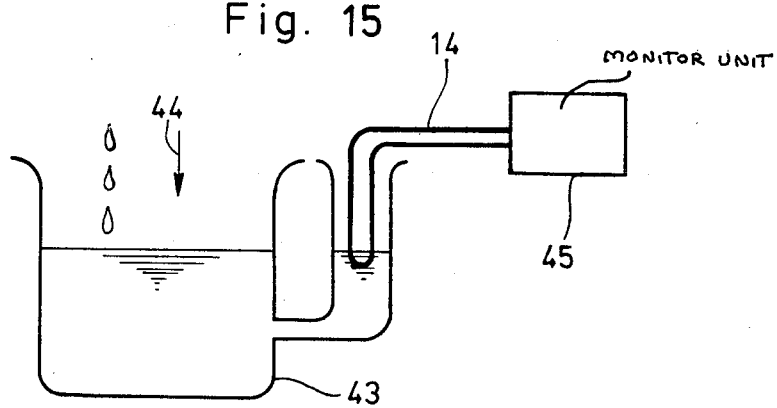
FIG. 15 is a schematic view used for the explanation of a fifth embodiment of the present invention.

The fourth embodiment may be equally applied, for example, in the detection of oil leakage in any piping system as shown in FIG. 15. In FIG. 15 an oil sump 43 is disposed at a location of a piping system of, for example a boiler in which leakage of the oil tends to occur very frequently. The oil detector cable 14 is folded back and the return portion is positioned at a predetermined height from the bottom of the oil sump 43. The ends of the oil detector cable 14 are connected to a monitor unit 45, including the light-emitting element 18, as well as the optical sensor 19 and their associated circuits, as described hereinbefore.

As the oil drops 44 accumulate in the oil sump 43 the liquid level in the sump 43 reaches the folded-back portion of the oil detector cable 14, as shown in FIG. 15. When this occurs, the monitor unit 45 gives a visual and/or an audio alarm in the manner described hereinbefore.

The modification of the fourth embodiment described above is adapted to be placed at such a position where the intermittent leakages of the oil in a very small quantity is inevitable, but immediate countermeasures are not needed until the oil that has leaked accumulates to a predetermined volume. That is, the detection response of the oil leakage detection system may be delayed.

Figure 16:
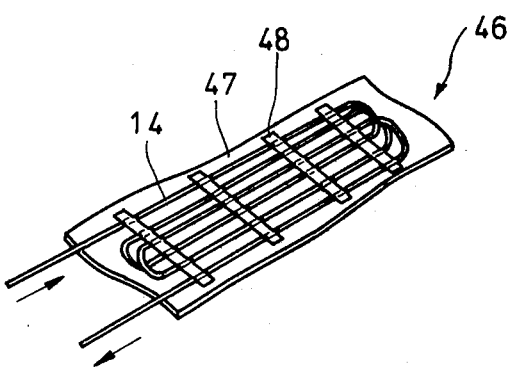

In the sixth embodiment of the present invention, as shown in FIG. 16, an oil detector mat 46 consists of the oil detector cable 14. The cable 14 is laid over an outer mat 47 in a zig-zag manner and securely attached thereto with adhesive tapes 48. The construction of the oil detector mat 46 will be described in more detail below.

The oil detector mat 46 is directly wrapped around a pipe, or the like, at a location where the oil leakage tends to occur, so that even an extremely small oil leakage may be immediately detected.

The mat 47 which is fabricated of soft materials such as fabrics, not only may facilitate the mounting of the oil detector cable 14 on a pipe or any other object from which the oil will leak or is expected to leak, but also may protect the oil detector cable 14 from damage by external forces. The surface area of the outer mat 47 is dependent upon the dimensions of an installation space; that is, dependent upon the diameter and thickness of flanges of pipes as will be described below.

Figure 17:
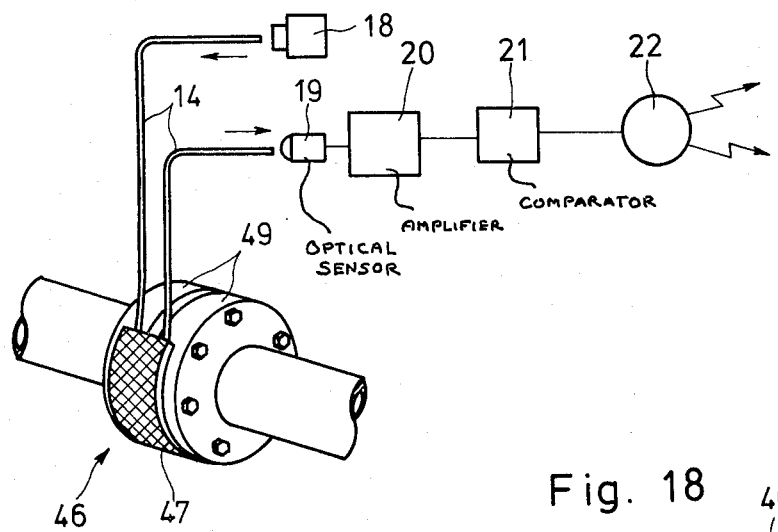

As shown in FIG. 17, the oil detector mat 46 can be used to detect the oil leakage from the joints between flanges 49 of the joined pipe sections. The oil detector mat 46 is partly wrapped on the flanges 49 so as to cover the lower halves thereof because the oil leaking through the joint between the flanges 49 tends to collect at the bottom of the joint.

As described above, the outer mat 47 is flexible so that the oil detector mat 46 may be brought into very close contact with the flanges 49 regardless of their diameters. The oil detector mat 46 may be bonded to the flanges 49 with suitable adhesives or made fast with bands or adhesive tapes. If the oil detector mat 46 is large enough to completely be wrapped around the flanges 49, the oil detector mat 46 may be securely attached to them by wrapping the oil detector mat 46 by any suitable tapes.

When the oil leaks through the joint between the flanges 49 and adheres to the oil detector cable 14, the intensity of light ray intercepted by the optical sensor 19 drops as described hereinbefore so that the alarm device 22 is activated to give visual and/or audio alarms.

Figure 18:
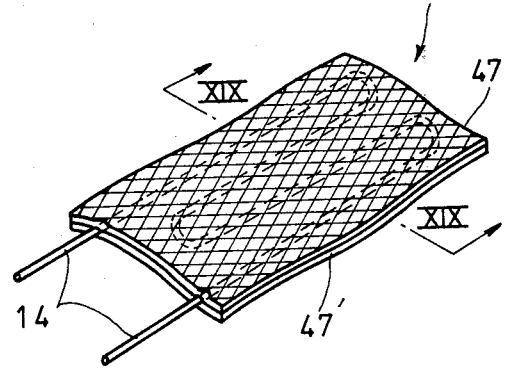
Figure 19:
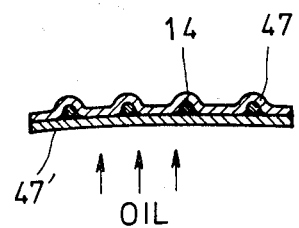

In FIGS. 18 and 19 a modification of the oil detector mat 46 is shown which further includes an inner mat 47' which is made of soft, flexible and oil-absorbing materials such as fabrics, felt or the like. The oil detector cable 14 is sandwiched between the outer and inner mats 47 and 47'. Since the inner mat 47' may readily absorb the oil that leaks through the joint between the flanges 49, the leaked oil immediately adheres to the oil detector cable 14 so that the oil leakage detection may be much facilitated. In addition, the inner mat 47' may avoid the direct contact of the oil detector cable 14 with the flanges 49 or any other objects on which the oil detector mat 46 is attached, so that damage to the oil detector cable 14 may be avoided. When the outer mat 47 is made of materials, such as leather, which are not pervious to the oil, the leaked oil may be spread over a wide space.

The outer mat 47 may be also made of materials which are not pervious to the oil even when the oil detector mat 46 has no inner mat 47' (FIG. 16).

The oil detector cable 14 is shown as being laid in a zig-zag form, but it will be understood that it may be laid in any suitable configurations. For instance, it may be laid in a spiral form.

In the seventh embodiment, a plurality of oil detectors 50 are interconnected to form an annular oil detection fence as shown in FIG. 20. Each oil detector 50 has a casing or housing 36 at one end and a plurality of cylindrical floats 51 which are fitted over protective jacket 37' and spaced apart from each other by a suitable distance as shown in FIGS. 20 and 21, the other end of the oil detector being attached to a float 51. It is to be understood that the number and shape of the floats 51 are not limited to those shown, as long as the oil detection fence may have suitable buoyancy. The casing 36 in which are encased the light-emitting element 18, the optical sensor 19 and the amplifier 20 as described hereinbefore is connected to the float 51 at the other end of an adjacent oil detector 50 with a connecting wire 52 so as to form a ring-shaped oil detection fence shown in FIG. 20. The oil detection fence may be placed on any area on the sea, river or lake, or in a harbor so as to monitor the water contamination with the oil.

The detail of the oil detector 50 is shown in FIG. 22. The oil detector cable 14 is folded back and sheathed in the protective jacket 37'. Both the ends of the oil detector cable 14 are extended out of one end of the protective jacket 37' and are optically connected to the light-emitting element 18 and optical sensor 19 in the casing 36, as described hereinabove.

The ends of the oil detector cable 14 are attached to the female connectors 24a and 24b. The female connectors 24a and 24b are connected to the light-emitting element 18 and optical sensor 19. The light ray emitted from the light-emitting element 18 enters the light guide of the oil detector cable 14 through the connector 24a, travels through the light guide and emerges at the other end of the light guide so as to be intercepted through the female connector 24b by the optical sensor 19 which, in turn, converts the light signal into the electric signal. The output from the optical sensor 19 is amplified by the amplifier 20 and is delivered to the monitor station 42.

When the leaked oil reached the oil detector cable 14, it passes through the sheath and the cladding and adheres to the exterior surface of the light guide core. Then the intensity of the light rays received by the optical sensor 19 drops as described hereinbefore so that the output signal from the amplifier 20 also drops in intensity or level. In response to the variation in output signal from the amplifier, the oil contamination alarm signal is generated. The casing must be made water proof, as it floats on the water.

The monitor station 42 is installed on the ground or on a ship and receives the output signal from the amplifier 20 through a wire or wireless transmission line. The signal is compared in the comparator 21 with a reference signal that is received, and in response to the output from the comparator 21 the alarm device 22 is activated to give visual and/or audio alarms.

The oil detection fence shown in FIG. 20 may be so assembled as to surround a tanker which is commencing unloading crude oil, or a tanker which carries the crude oil to its full capacity and is anchored as a floating storage tank, or an underwater oil storage installation. Therefore, even when a small quantity of oil leaks from a tanker or an underwater oil storage tank, the alarm device 22 immediately gives an alarm.

When the oil detection fence is used for the detection of oil leakages from an underwater oil storage installation such as an underwater tank, the buoyancy of the floats 51 may be so adjusted that the oil detection fence may be sunk in the water at a suitable level from the bottom of the sea or the like and anchored to the underwater oil storage installation.

Figure 23:
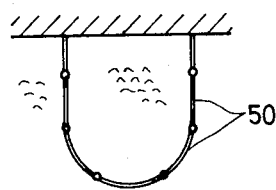
FIG. 23 is a view used for the explanation of an eighth embodiment of the present invention.

In the embodiment shown in FIG. 23, the oil detectors 50 are so connected as to form a U-shaped oil detection fence which may be installed adjacent to a cliff or a beach so as to detect the water contamination with the oil.

Figure 24:
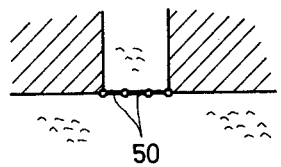
FIG. 24 is a view used for the explanation of a ninth embodiment of the present invention.

In the embodiment shown in FIG. 24, the oil detectors 50 are connected straight across the mouth of a river, or at a discharge opening of industrial and domestic wastes.

Figure 25:
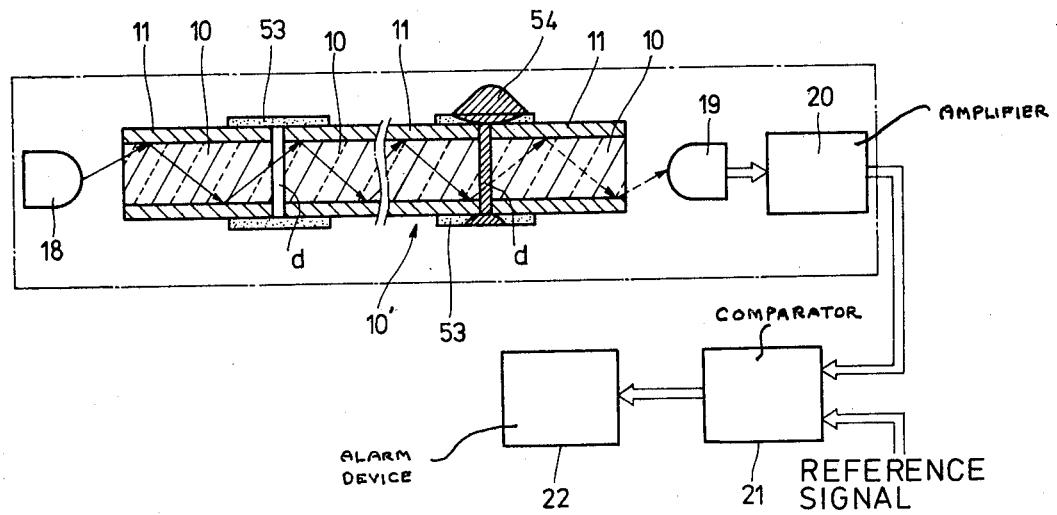
FIG. 25 is a view used for the explanation of a tenth embodiment of the present invention.

A light guide 10' shown in FIG. 25 consists of a plurality of relatively short light guide cores 10 and claddings 11 and a plurality of light guide connectors 53. The light guide connectors 53 are made of liquid-absorbing materials and adapted to concentrically join the adjacent light guides 10' in such a way that the opposing ends of the adjacent light guides 10' may be spaced apart from each other by a predetermined distance d. As with the other embodiments, one end of the thus assembled oil detector is optically coupled to the light-emitting element 18 while the other end, to the optical sensor 19. When no oil fills the space d between the ends of the adjacent light guides 10', the propagation of a light ray from the light emitting element 18 to the optical sensor 19 is not disturbed so that the optical sensor 19 receives the light rays at a predetermined intensity or within a predetermined range of intensity. However, when the oil 54 is absorbed by the connector 53 and consequently fills the space d between the ends of the adjacent light guides 10', the intensity of the light rays intercepted by the optical sensor 19 considerably drops below a predetermined level because the energy of the light ray is absorbed when it passes through the oil filled in the hatched space.

As described hereinabove the light signal received by the optical sensor 19 is converted into an electrical signal, which is amplified by the amplifier 20. The output from the amplifier 20 is applied to the comparator 21 so as to be compared with a reference signal. When the output from the amplifier 20 is lower in level than the reference signal, the comparator 20 delivers an output representing the detection of the leaked oil 54 to the alarm device 22 which in turn is activated to give visual and/or sound alarms; that is, a display lamp is turned on and/or a buzzer is activated.

So far the present invention has been described as being used for the detection of the leaked oil, but it is to be understood that the present invention may be equally used for the detection of leakages of any other liquids. Furthermore, it is also to be understood that various modifications may be made without departing from the true spirit of the present invention. For instance, instead of stranding or otherwise assembling a large number of light guides into a cable, a single or a few light guides may be used when satisfactory protection means may be provided and/or if physical and chemical properties of the light guides used may permit such an arrangement as described above. The cladding and the sheath may be made of any suitable materials which may be highly pervious to and easily swollen by a liquid whose leakage is to be detected. It is preferable that the protective jacket may be made of materials which exhibit strong resistance against the externally applied forces and corrosion, and is water-proof, as well. Furthermore, it is also understood that the light guides can be used without the sheath and the protective jacket.

The novel features, effects and advantages of the present invention may be summarized as follows:

(I) Leakages of not only oil but also any other liquids may be automatically detected in terms of the variation of the intensity of light rays intercepted by the optical sensor or light receiver so as to give alarms. Thus, the liquid leakage detection system of the present invention is very fast in response and highly reliable and dependable in operation so that hazards due to the leakage of oil or other liquids may be prevented.

(II) The higher the number of detector cables, mat or detectors, the more accurately a leaking location or point may be detected.

(III) Materials of the sheath and mat may be so selected that the liquid leakage detection system may quickly and correctly respond to a specified liquid, the leakage of which is to be detected.

(IV) The liquid leakage detection system of the present invention may be easily placed on any existing installations.

(V) Since the sheath and protective jacket are very flexible, the cables, mat and detectors may be applied to any objects in any configurations in a simple manner.

What is claimed is:

1. A liquid leakage detection system comprising a plurality of light guides each being provided with a relatively straight light guide core that has a predetermined index of refraction and a cladding which is an outer layer wholly surrounding said light guide core, said cladding having an index of refraction lower than that of said light guide core and is adapated to be swelled by a liquid whose leakage is to be detected, said light guides being stranded into a detector cable and being provided with a covering sheath, the ends of said light guide core being uncoated so that a light ray entering into said light guide core at one end thereof may emerge from the other end thereof with a minimum transmission loss, a light-emitting element optically coupled to one end of said detector cable, an optical sensor optically coupled to the other end of said detector cable, and an electrical circuit for deriving the output signal whose level or intensity is in proportion to the intensity of the light rays intercepted by said optical sensor whereby the liquid leakage may be detected in terms of the drop in the intensity of the light rays intercepted by said optical sensor due to the adhesion of said liquid to said cladding.

2. A liquid leakage detection system as set forth in claim 1 further comprising a liquid storage tank, and a plurality of said detector cables being disposed in the form of a mesh.

3. A liquid leakage detection system as claimed in claim 1 wherein at least one detector cable is disposed in the foundation of a liquid storage tank whereby said detector cable is in intimate contact with the outer wall surface of said liquid storage tank.

4. A liquid leakage detection system as claimed in claim 1 further comprising a pipe line and at least one detector cable extending along said pipe line.

5. A liquid leakage detection system as claimed in claim 1 further comprising a sump, and wherein said detector cable is positioned in said sump for receiving a leaking liquid.

6. A liquid leakage detection system as claimed in claim 1 further comprising a flexible mat, said detector cable being positioned over said mat in such a configuration that said detector cable may be substantially uniformly distributed over one major surface thereof, and said mat with said detector cable being secured to an object of said liquid detection.

7. A liquid leakage detection system as set forth in claim 1 wherein said detector cable is provided with a protective tube in the form of a sheath which is provided with a plurality of floats to thereby provide an oil detector, and a plurality of said oil detectors being interconnected to form a fence.

8. A liquid leakage detection system as claimed in claim 1 further comprising detector cable connector means, said plurality of detector cables being connected in series with said detector cable connector means in such a manner whereby the ends of said adjacent detector cable may be spaced apart from each other by a predetermined distance, said detector cable connector means being fabricated of material pervious to said liquid.

9. A liquid leakage detection system as set forth in claim 6 wherein said detector cable on said first mat is further covered with a second flexible mat, said first mat being made with materials which are pervious to said liquid while said second mat is made of materials which are not pervious to said liquid or vice versa, and said detector cable is positioned so as to sandwich itself between said first and second mats.

* * * * *